United States Patent [19]

Zaiger

[11] Patent Number: Plant 5,641

[45] Date of Patent: Jan. 21, 1986

[54] PEACH TREE-'JUNE CREST'

[76] Inventor: Chris F. Zaiger, 537 Rosemore Ave., Modesto, Calif. 95351

[21] Appl. No.: 432,664

[22] Filed: Nov. 14, 1983

[51] Int. Cl.[4] ..... A01H 5/00
[52] U.S. Cl. ..... Plt./43
[58] Field of Search ..... Plt./43

*Primary Examiner*—James R. Feyrer

[57] ABSTRACT

A new and distinct variety of peach tree which is of large size, vigorous and upright in growth; the tree being a regular and productive bearer of large, yellow flesh, early ripening, clingstone fruit having yellow skin color overspread with a high degree of red. The fruit is further characterized by its good eating quality, firm fresh with good storage life and the ability to ship to long distance markets.

1 Drawing Figure

ORIGIN OF THE VARIETY

The new variety of peach tree was originated by me in my experimental orchard at Modesto, Calif. This peach tree was selected from a large group of seedlings grown from a cross between Fayette peach (non-patented) and a seedling of unkown parentage. The selection was maintained under careful and continual observation, during which time it was selected for reproduction, due to its distinct and desirable characteristics.

ASEXUAL REPRODUCTION OF THE VARIETY

The present variety of peach tree was asexually propagated by budding as performed by me in my experimental orchard at Modesto, Calif. and shows that said characteristics described above proved identical with the original peach tree and are established and transmitted through succeeding propagations.

SUMMARY OF THE VARIETY

The herein variety of peach tree is of large size, vigorous upright growth and a regular productive bearer of large size, early ripening, yellow flesh, clingstone fruit having a high degree of red skin color and greater firmness than the present commercial varieties within this ripening period. The ripening period being approximately 2 to 3 days later than Spring Crest peach, (non-patent).

PHOTOGRAPH OF THE VARIETY

The accompanying photographs show typical specimens of the foliage and fruit of my new variety, with upper and lower surfaces of the leaves being illustrated and a fruit divided on its suture plane showing flesh coloration with a stone remaining in place. The illustrations were taken shortly after being picked at maturity, (shipping ripe) and the colors are as nearly true as reasonably possible in color representations of this type.

DESCRIPTION OF THE VARIETY

The following is a detailed botanical description of the foliage and fruit of my new peach variety, as based upon observations of specimens grown at Modesto, Calif., with color terminology (except those in common terms) in accordance with Reinhold Color Atlas by A. Korneruf and J. H. Wanscher.

Tree:

*Size.*—Large.
*Vigor.*—Vigorous.
*Form.*—Upright.
*Production.*—Productive.
*Bearing.*—Regular.

Trunk:
*Size.*—Medium to stocky.
*Surface.*—Medium to shaggy.

Branches:
*Size.*—Medium to stocky.
*Surface.*—Medium shaggy.
*Color.*—New Growth reddish brown. Mature growth, brown to grayish brown.
*Lenticels.*—Medium size. Medium quantity.

Leaves:
*Size.*—Medium. Average length — $6\frac{1}{4}''$. Average with — $1\frac{3}{8}''$.
*Form.*—Lanceolate; acutely pointed.
*Thickness.*—Medium.
*Texture.*—Smooth.
*Margin.*—Crenate.
*Petiole.*—Average length — $\frac{1}{2}''$. Average width — 1/16 to 3/32". Longitudinally grooved.
*Glands.*—Globose. Number one to four — mostly opposite and alternate. Positioned on base of leaf blade and upper part of petiole.
*Color.*—Upper surface — deep green (28-E-7) to (28-E-8). Lower surface — Grayish green (29-E-5) to (29-D-5).

Flower buds:
*Size.*—Medium.
*Length.*—Medium.

Flowers:
*Blooming period.*—Mar. 1, 1979 to Mar. 11, 1979.
*Size.*—Large, showy.

Fruit:
*Maturity when described.*—Hard ripe.
*Date of first picking.*—June 5, 1979.
*Date of last picking.*—June 12, 1979.
*Size.*—Comparatively uniform. Large. Average transversely in suture plane $2\frac{1}{2}''$. Average diameter axially $2\frac{1}{2}''$.
*Form.*—Nearly globose. One half slightly larger at suture plane.
*Suture.*—Shallow but distinct, extends from base to apex.
*Ventral surface.*—Varies from equal to unequal.

*Cavity.*—Rounded. Average depth. — $\frac{1}{2}''$. Average breadth — 1".

*Apex.*—Short to slighty retuse.

Skin:

*Thickness.*—Medium.

*Texture.*—Tough. Tenacious to flesh.

*Tendency to crack.*—None.

*Down.*—Scant, very short.

*Color.*—Bright yellow ground color (4-A-8) to (5-A-6). Red bush covering most of surface (7-A-8) to (9-B-8).

Flesh:

*Juice.*—Moderate.

*Texture.*—Firm, meaty.

*Ripens.*—Uniform.

*Amygdalin.*—Undetected.

*Flavor.*—Mild.

*Aroma.*—Distinct.

*Eating quality.*—Good.

*Color.*—Yellowish orange (4-A-8). Golden yellow (5-A-7).

Stone:

*Type.*—Clingstone: Adheres to flesh over entire surface.

*Size.*—Medium to large. Average length — $1\frac{1}{2}''$. Average width — $1\frac{1}{8}''$. Average thickness — $\frac{3}{4}''$.

*Form.*—Ovid.

*Base.*—Mostly straight.

*Apex.*—Acute.

*Sides.*—Mostly equal.

*Surface.*—Irregularly furrowed toward apex, pitted toward base.

*Color.*—Light brown (8-D-7) to (8-C-7).

*Tendency to split.*—Very Slight.

Use: Market, local and long distance. Dessert.

Shipping and keeping quality: Very Good.

The peach tree and its fruit herein described may vary in slight detail due to soil and climatic conditions under which this peach tree may be grown; the present description being of the variety as grown in Modesto, Calif.

The following is claimed:

1. A new and distinct variety of peach tree, as shown and described, of large size, upright, vigorous growth and a regular productive bearer of large, yellow flesh, early maturing, clingstone fruit with a high degree of red skin color and the firm flesh being of good eating and shipping quality.

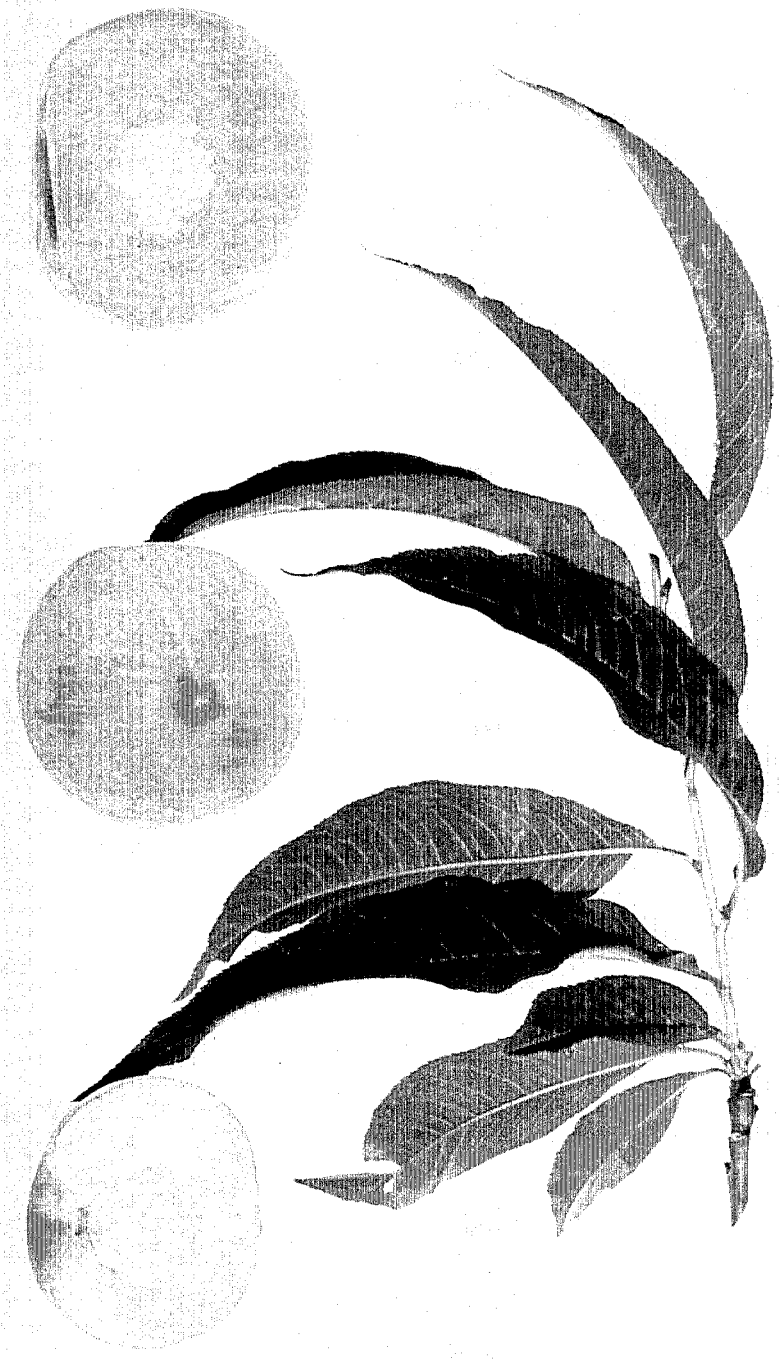

* * * * *